United States Patent
Hoffman et al.

(10) Patent No.: US 8,372,073 B2
(45) Date of Patent: *Feb. 12, 2013

(54) MULTI-PIN CLAMP AND ROD ATTACHMENT

(75) Inventors: Mindy Lynn Hoffman, Pottstown, PA (US); Charles Dean Preston, II, Fort Walton Beach, FL (US); Michael Charles Mazzio, Schwenksville, PA (US)

(73) Assignee: Sythes USA, LLC, West Chester, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/715,797

(22) Filed: Mar. 2, 2010

(65) Prior Publication Data

US 2010/0160972 A1  Jun. 24, 2010

Related U.S. Application Data

(63) Continuation of application No. 10/402,897, filed on Mar. 28, 2003, now Pat. No. 7,699,848, which is a continuation of application No. 09/736,753, filed on Dec. 14, 2000, now Pat. No. 6,565,564.

(51) Int. Cl.
*A61B 17/00* (2006.01)
(52) U.S. Cl. ........................................................ 606/59
(58) Field of Classification Search .................. 606/54, 606/57–59, 250–253
See application file for complete search history.

(56) References Cited

U.S. PATENT DOCUMENTS

| | | | | | |
|---|---|---|---|---|---|
| 4,483,334 | A | * | 11/1984 | Murray | 606/59 |
| 4,620,533 | A | * | 11/1986 | Mears | 606/54 |
| 5,624,440 | A | * | 4/1997 | Huebner | 606/59 |
| 5,662,648 | A | * | 9/1997 | Faccioli et al. | 606/54 |
| 5,709,685 | A | * | 1/1998 | Dombrowski et al. | 606/278 |
| 5,746,741 | A | * | 5/1998 | Kraus et al. | 606/54 |
| 5,752,954 | A | * | 5/1998 | Mata et al. | 606/59 |
| 5,891,144 | A | * | 4/1999 | Mata et al. | 606/59 |
| 5,961,515 | A | * | 10/1999 | Taylor et al. | 606/59 |
| 6,022,348 | A | * | 2/2000 | Spitzer | 606/54 |
| 6,277,119 | B1 | * | 8/2001 | Walulik et al. | 606/57 |
| 6,342,054 | B1 | * | 1/2002 | Mata | 606/59 |
| 6,702,814 | B2 | * | 3/2004 | Walulik et al. | 606/57 |

* cited by examiner

*Primary Examiner* — Eduardo C Robert
*Assistant Examiner* — Mary Hoffman
(74) *Attorney, Agent, or Firm* — Fay, Kaplun & Marcin, LLP

(57) ABSTRACT

A fixation rod clamp is for coupling a bone pin locking assembly to a bone fixation rod. The clamp comprises a rod attachment portion including a jaw portion and a coupling portion, the jaw portion having first and second opposing jaws extending in a first direction, the jaws forming an opening there between configured to receive the bone fixation rod, the coupling portion extending from the jaw portion in a second direction; and a coupling having a pin vise cooperating portion to engage the bone pin locking assembly and a clamp cooperating portion configured to receive the coupling portion. The jaw portion is configured to engage the bone fixation rod when the bone fixation rod is located within the opposing jaws to thereby mechanically couple the bone pin locking assembly to the bone fixation rod.

11 Claims, 8 Drawing Sheets

MULTI-PIN CLAMP AND ROD ATTACHMENT

CROSS-REFERENCE TO RELATED APPLICATIONS

This application is a Continuation of U.S. patent application Ser. No. 10/402,897 filed on Mar. 28, 2003 which is a continuation of U.S. patent application Ser. No. 09/736,753 filed on Dec. 14, 2000 (now the U.S. Pat. No. 6,565,564). The disclosures of these applications are incorporated herein by reference.

TECHNICAL FIELD

The present invention relates to a traumatologic device, and, more particularly, to an improved traumatologic device for reducing long-bone fractures that require external fixation.

BACKGROUND OF THE INVENTION

A variety of traumatologic devices for reduction of bone segments are known in the art. For example external bone fixation devices (commonly referred to as external fixators) are known. Typically external fixators are used to reduce fractures of the long bones in the human body. These devices are always placed in position under anesthesia. In order to reduce the duration of the anesthesia, fixator devices have been developed to allow positioning at every possible angle, while still allowing easy adjustment by a surgeon.

The early development of external fixator devices, such as that exemplified by U.S. Pat. No. 2,250,417 to Ettinger, was aimed at producing a simple and lightweight fracture reduction device which is practical to leave in place to serve as a retention device, thereby rendering a cast unnecessary. As disclosed, the Ettinger device allows two separate sets of dual bone pins or screws, each transcutaneously installed in the bone on either side of a fracture, to be connected and fixed at variable points to a single bone fixation rod running roughly parallel to the longitudinal axis of the affected bone. This resultant connection of opposing pin/screw sets provides the immobilization necessary to allow proper healing of the fracture. Ettinger discloses the use of multiple sleeve and post connections between the bone pins/screws and the bone fixation rod to allow the bone pins or screws to be installed at varying angles relative to the bone fixation rod. Ettinger additionally discloses the use of a rod and sleeve configuration whereby one of the two bone pin/screw couplings is fixed to the bone fixation rod, while the second comprises an internally threaded sleeve that is threaded over the opposite end of the bone fixation rod, and whose position is adjustable relative to the fixed coupling via rotation of the bone fixation rod.

Later improvements on the Ettinger design, such as that disclosed by U.S. Pat. No. 4,135,505 to Day, allow for the installation of an increased and/or variable number of bone pins on each side of the fracture. This provides the advantage of giving the practitioner more options in the spacing of pins, and of avoiding installing a pin at a particular point on the bone if such placement was undesirable. The Day device additionally discloses a bone pin clamp incorporating a ball and socket connection to allow for varying bone pin installation angles.

Further improvements such as those disclosed by U.S. Pat. No. 5,160,335 to Wagenknecht, U.S. Pat. No. 5,219,349 to Krag, U.S. Pat. No. 5,624,440 to Huebner, U.S. Pat. No. 5,891,144 to Mata et al., and U.S. Pat. No. 6,022,348 to Spitzer disclose bone pin/screw clamps which incorporate more modern universal joint assemblies to allow easier adjustment of the distance between bone pin clamps along the length of the bone fixation rod when the attached bone pins/screws are installed at multiple angles relative to the immobilization rod. Moreover the Krag, Huebner, Mata et al., and Spitzer devices provide easier means to adjust the relative distance between bone pin couplings on opposing sides of a fracture (accomplished by simple sliding in the Krag, Huebner, Mata et al., and Spitzer devices, and by incremental rotation of an attached screw and nut combination in the Day and Wagenknecht devices). Yet a further improvement is disclosed in the Wagenknecht patent, which provides springs between the bone pin clamp faces to spread the faces and thereby facilitate introduction of the bone pins.

The difficulty with the Huebner, Krag, Wagenknecht and Day devices is that their means of fixing the bone pin clamp to the bone fixation rod is by way of a closed hole and screw combination. To facilitate installation of these fixators, the bone pin clamps must be threaded onto the bone fixation rod from one end of the rod, making installation cumbersome. The Mata et al., and Spitzer devices address this problem by providing bone pin clamps that attach to the bone fixation rod utilizing open-face jaws. This design allows the device to be engaged with the rod by simply placing it onto the desired location along the length of the rod, without the need for threading as in the Mata et al. and Spitzer devices. The difficulty with the Mata et al. and Spitzer devices is that their open-faced bone pin clamp jaws are two-piece designs which by their nature cannot be self-sprung and so require the use of an additional piece, such as a coil or compression spring, to maintain the jaws in an open position during installation onto the bone fixation rod. Additionally, the two piece nature of their design increases unit fabrication difficulty and cost.

Accordingly, there is a need in the art to provide a simpler design bone pin clamp assembly that minimizes the total number of steps an operator must take to engage the clamp assemblies and bone fixation rod, while still providing maximum flexibility to the operator in adjusting the distance between bone pin clamps on either side of a fracture.

SUMMARY OF THE INVENTION

The present invention provides a fixation rod clamp for coupling a bone pin locking assembly to a bone fixation rod. The clamp comprises a rod attachment portion having a jaw portion with a longitudinal axis and first and second opposing jaws configured to receive the bone fixation rod, and a coupling portion. The fixation rod clamp further comprises a coupling having a pin vise cooperating portion to engage the bone pin locking assembly and a clamp cooperating portion configured to receive the coupling portion of the rod attachment portion. The fixation rod clamp comprises a single piece, and the jaw portion of the fixation rod clamp is configured to engage the bone fixation rod when the bone fixation rod is pressed into the opposing jaws to mechanically couple the bone pin locking assembly to the bone fixation rod.

The first opposing jaw may further have a first spring constant and the second opposing jaw may further have a second spring constant, such that when at least one of the first and second opposing jaws is displaced from a rest position, a resulting spring force is generated in the at least one jaw, urging the displaced jaw back toward the rest position. The fixation clamp may further be configured so that when the bone fixation rod is inserted into the fixation rod clamp jaw portion, the spring force in the at least one opposing jaw contributes to the mechanical coupling of the bone pin locking assembly to the bone fixation rod. The fixation rod clamp may also be configured to have a locked position which substantially prevents movement of the clamp along the bone fixation rod. The fixation rod clamp may comprise a bolt disposed within and operatively associated with the fixation rod clamp jaw portion, wherein tightening of the bolt configures the clamp to the locked position.

The fixation rod clamp jaw portion may engage the bone fixation rod when the rod is pressed into the jaw portion in a direction substantially along the longitudinal axis of the jaw portion.

A fixation member clamp may be provided for coupling a bone fixation member to a locking assembly, the member clamp comprising a first fixation member clamp portion having a jaw portion with a longitudinal axis and first and second opposing jaws configured to receive the bone fixation member. The member clamp may also comprise a first coupling portion configured to engage the locking assembly. The first fixation member clamp portion may comprise a single piece, and the jaw portion may be configured to engage the bone fixation member when the fixation member is pressed into the opposing jaws to thereby mechanically couple the locking assembly to the bone fixation member.

The locking assembly may further comprise a second fixation member clamp portion having a jaw portion with a longitudinal axis and first and second opposing jaws configured to receive a second bone fixation member. The locking assembly may further comprise a second coupling portion configured to engage the first coupling portion of the member clamp. The fixation member clamp portions each may comprise a single piece, and the jaw portion of each clamp portion may be configured to engage one of the bone fixation members when the associated bone fixation member is pressed into the opposing jaws to thereby mechanically couple the fixation member clamp portion to the associated bone fixation member.

The first and second opposing jaws of the single-piece fixation clamp portion may have a clearance therebetween that is slightly smaller than an outside diameter of the bone fixation member such that an interference is established between the opposing jaws and the fixation member when the fixation member is initially installed into the jaw portion.

The first and second opposing jaws may further have respective first and second spring constants, so that when at least one of the first and second opposing jaws is displaced from a rest position, a resulting spring force is generated in the at least one jaw, urging the jaw back to the rest position. The fixation member clamp may further be configured so that when the fixation member is pressed into the jaw portion, the spring force contributes to the mechanical coupling of the locking assembly to the bone fixation member.

The fixation member clamp may also be configured so that the jaw portion engages the bone fixation member when the fixation member is pressed into the jaw portion in a direction substantially along the longitudinal axis of the jaw portion. The fixation member clamp of this embodiment may be capable of being immobilized along the first bone fixation member without freedom to rotate or move, and further a bolt may be disposed within and operatively associated with the fixation rod clamp jaw portion, wherein tightening of the bolt configures the clamp to the locked position.

A pair of fixation member clamps may be provided for coupling first and second bone fixation members, the clamps comprising first and second fixation member clamps, each clamp comprising a jaw portion having a longitudinal axis and first and second opposing jaws configured to receive a bone fixation member. Each clamp may further comprise a coupling portion, the coupling portions of the first and second fixation member clamps may be configured and arranged to engage each other to provide at least one degree of relative rotational freedom. At least one of the jaw portions may comprise a single piece, the at least one jaw portion configured to engage the first or second bone fixation member when the fixation member is pressed into its opposing jaws to thereby mechanically couple the bone fixation member to the at least one respective fixation member clamp.

At least one of the fixation member clamps of this embodiment may have first and second opposing jaws which have a clearance therebetween that is slightly smaller than an outside diameter of the respective bone fixation member such that an interference is established between said opposing jaws and the bone fixation member when the bone fixation member is initially installed into the single-piece jaw portion. The at least one fixation member clamp first and second opposing jaws may have respective first and second spring constants so that when at least one of the first and second opposing jaws is displaced from a rest position, a resulting spring force is generated in the at least one jaw, urging the displaced jaw back toward the rest position, and the spring forces may contribute to the mechanical coupling of the fixation member clamp to the bone fixation member.

The jaw portion of the at least one fixation member clamp may engage the associated bone fixation rod when the rod is pressed into the jaw portion in a direction substantially along the longitudinal axis of the jaw portion. One of the fixation member clamps may be capable of being immobilized along its associated bone fixation rod without freedom to rotate or move. A bolt may be disposed within and operatively associated with jaw portion of the at least one fixation member clamp, so that tightening of the bolt locks the position of the clamp.

In an alternative embodiment, a fixation member clamp may be provided for coupling to a first bone fixation member. The clamp may comprise a fixation member attachment portion having a jaw portion and a coupling portion. The jaw portion may have a longitudinal axis and first and second opposing jaws configured to receive the first bone fixation member. The coupling portion may be configured to engage a locking assembly, the locking assembly comprising a coupling portion associated with the coupling portion of the fixation member attachment portion. The locking assembly may further comprise a locking portion configured to engage a second bone fixation member. Further, the jaw portion may comprise a single piece and be configured to engage the first bone fixation member when the member is pressed into the opposing jaws of the jaw portion to mechanically couple the bone fixation member to the locking assembly.

The single-piece fixation member clamp first and second opposing jaws may have a clearance therebetween which is slightly smaller than an outside diameter of the bone fixation member such that an interference is established between the opposing jaws and the bone fixation member when the bone fixation member is initially installed into the jaw portion. At least one of the fixation member may comprise a bone fixation rod, and the locking assembly may comprise a bone pin locking assembly.

The coupling portions of the fixation member attachment portion and the locking assembly may be configured to allow at least one degree of rotational freedom of the jaw portion with respect to the locking assembly. The coupling portions may further be configured to allow at least two degrees of rotational freedom of the fixation member clamp with respect to the locking assembly. The coupling portions of the fixation member attachment portion and the locking assembly may also comprise corresponding serrations to prevent relative rotation of the member attachment portion and the locking assembly when the serrations of the respective coupling portions are engaged.

The coupling portion of either the fixation member attachment portion or the locking assembly may comprise a spring, and the other may comprise a bore configured to accept the spring. The coupling portions may be further configured so that the spring tends to separate the corresponding serrations to permit relative rotation of the fixation member attachment portion and the locking assembly.

BRIEF DESCRIPTION OF THE DRAWINGS

The features and advantages of the present invention will become more readily apparent from the following detailed description of the invention in which like elements are labeled similarly and in which.

DETAILED DESCRIPTION OF THE PREFERRED EMBODIMENTS

The traumatological device of the present invention is discussed herein with reference to a preferred embodiment adapted to be used in the consolidation and fixation of a fractured long bone. It is to be understood that the invention finds applicability for use in any circumstance in which it is desired to fix the orientation of bone segments on either side of a fracture.

Figure 1A:
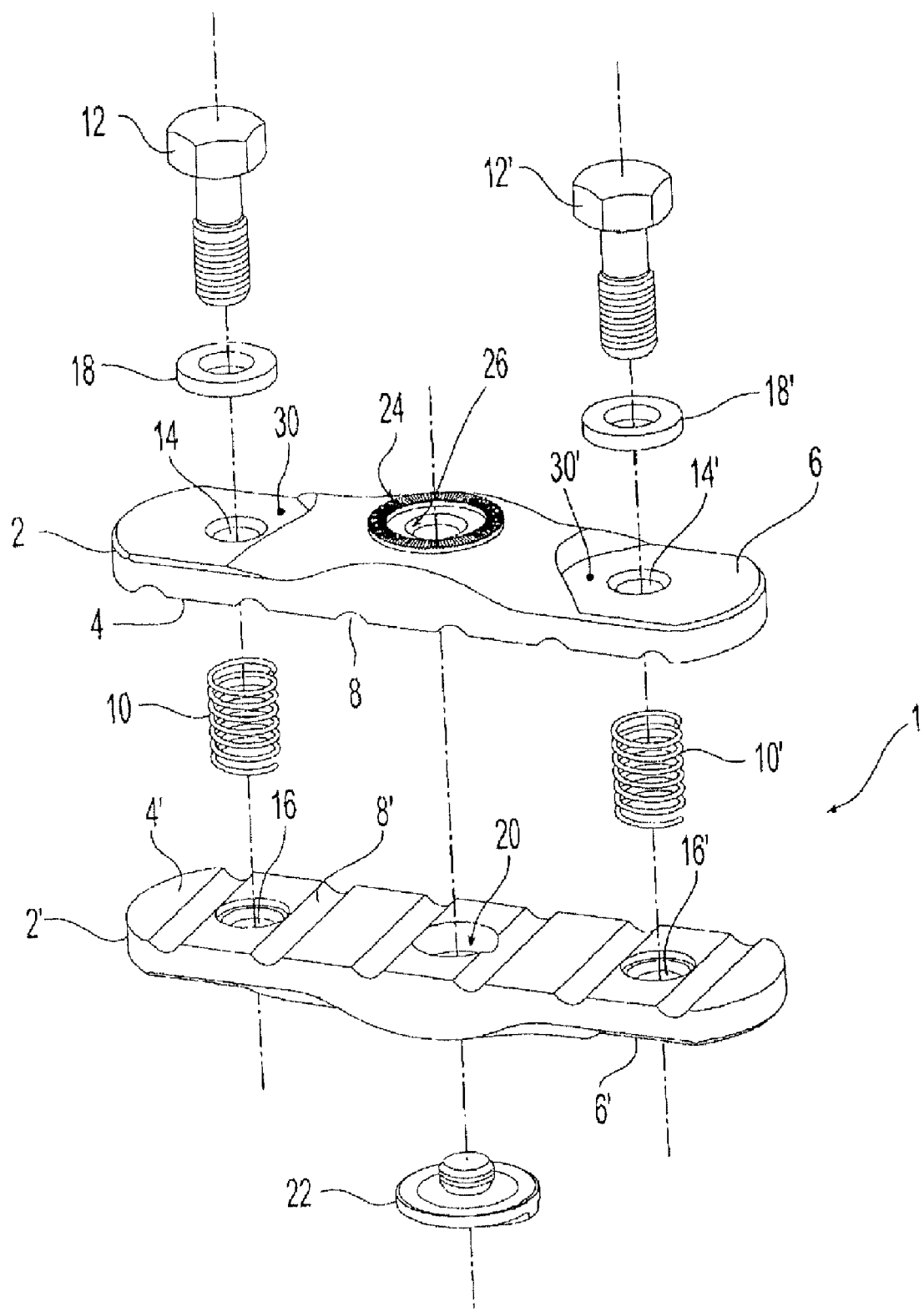
FIGS. 1A, 1B and 1C are two exploded perspective views and an elevation view of a bone pin vise portion, a bone pin vise opposing plate and star grind cover, and a bone pin vise opposing plate incorporating triangular bone pin clamping grooves, respectively, of the bone pin locking assembly of the current invention.
Figure 6:
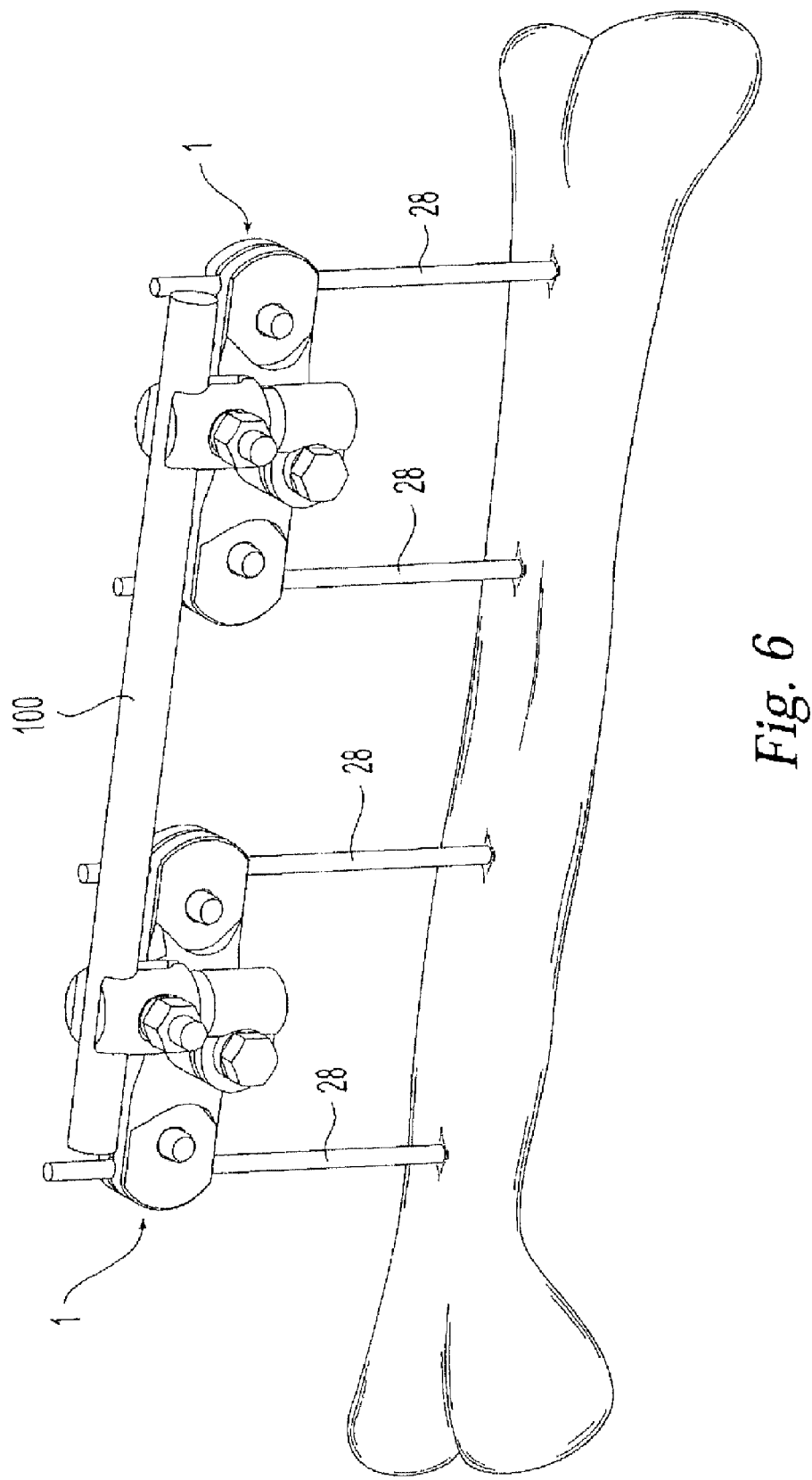
FIG. 6 is a perspective view of a complete bone fixation device installed on a bone.

Referring more particularly to the drawings, FIG. 1A shows an exploded view of a bone pin vise portion. As shown in FIG. 1A, the bone pin vise portion 1 comprises first and second opposing plates 2 and 2' with engaging faces 4 and 4', and outside faces 6 and 6'. Each engaging face is characterized by a plurality of spaced parallel grooves 8 and 8' which are cylindrically arcuate and which are in confronting relation to the spaced parallel grooves on the face of the opposite plate. The parallel grooves 8 and 8' coordinate to receive the proximal ends of bone pins 28 (shown in FIG. 6) installed on one side of a fractured bone. When the pin vise portion is in the clamped condition, the bone pins 28 are nested in the respective grooves formed by the conjunction of parallel grooves 8 and 8' (of engaging faces 4 and 4'). It will be understood that the number and shape of the grooves is not critical to the operation of the device.

The opposing plates 2 and 2' are connected by two vise bolts 12 and 12' which operate to draw together engaging faces 4 and 4' in order to grip the proximal ends of bone pins 28 which have been installed in a bone. Vise bolts 12 and 12' are slideably accepted by corresponding bores 14 and 14' in each end of first opposing plate 2, and are threadably accepted by threaded bores 16 and 16' in each end of second opposing plate 2'. The internal threads of bores 16 and 16' of second opposing plate 2' correspond with the external threads of vise bolts 12 and 12' such that a clockwise rotation of vise bolts 12 and 12' acts to draw opposing plates 2 and 2', and therefore engaging faces 4 and 4', together. Further, first opposing plate 2 incorporates bolt head bearing surfaces 30 and 30' to provide uniform bearing contact with the bottoms of the heads of pin vise bolts 12 and 12'. The vise bolts 12 and 12' may be provided with washers 18 and 18' positioned between the heads of the vice bolts 12 and 12', and bolt head bearing surfaces 30 and 30' of the pin vise portion opposing plate 2. The washers serve to reduce friction between the vise bolts and bolt head bearing surfaces, thereby easing final tightening of the vise bolts.

Preferably, the vise bolts 12 and 12' will be initially fit with the washers 18 and 18', then installed in the opposing plates, followed by a "loose-fit" tightening to the point that only a small clearance remains between the cylindrical voids formed by the plurality of spaced parallel grooves 8 and 8' and the outside surfaces of the cylindrical bone pins 28. In this way the pin vise portion 1 may easily be slipped onto the bone pins 28, such that during the surgical procedure only minor additional tightening of the vise bolts 12 and 12' will be required to firmly fix the bone pins 28 within the bone pin vise portion 1.

Figure 3:
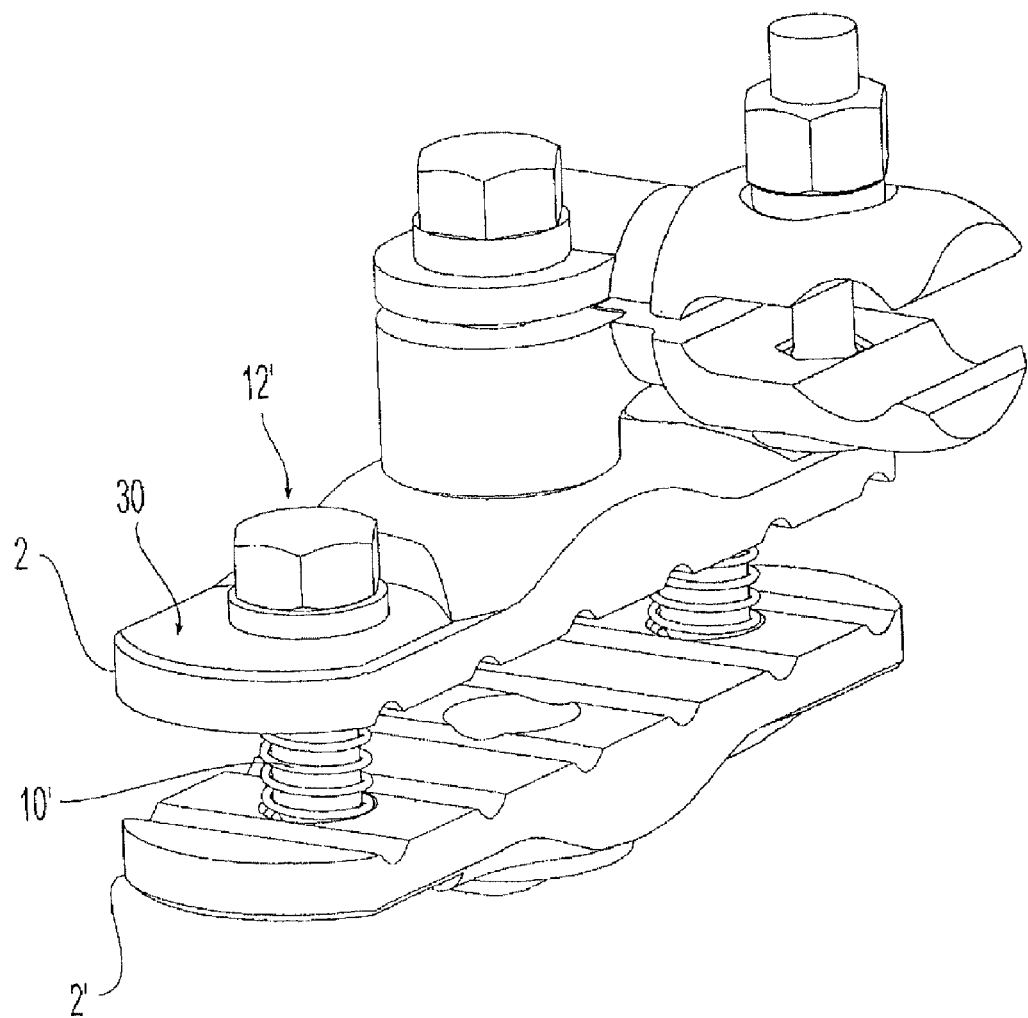
FIG. 3 is a perspective view of an assembled bone pin vise portion of FIG. 1 connected to an assembled rod attachment portion of FIG. 2.

In a preferred embodiment, the pin vise portion opposing plates 2 and 2' incorporate coil springs 10 and 10' between engaging faces 4 and 4' to forcibly separate engaging faces 4 and 4'. The provision of this separating force holds the plates apart during installation of the pin vise portion onto the bone pin proximal ends, easing such installation. To this end, cylindrical coil springs 10 and 10' are installed about the shafts of vise bolts 12 and 12' such that vise bolt shafts are slidably received by the bore formed within the inside diameter of each coil spring 10 and 10' (see FIG. 3).

Figure 2:
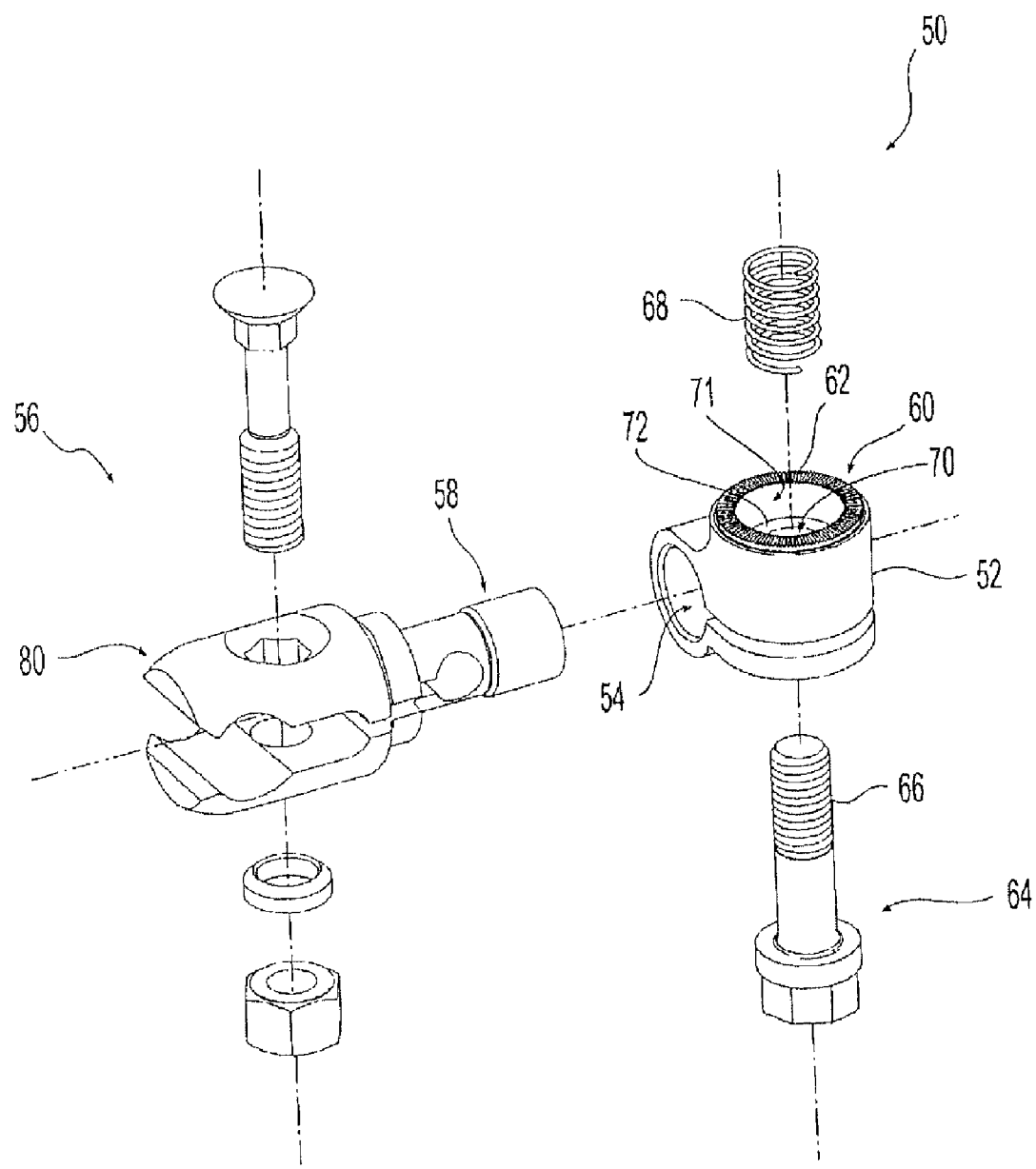
FIG. 2 is an exploded perspective view of a rod attachment portion of the bone pin locking assembly of the current invention.

FIG. 2 shows an exploded view of a rod attachment portion 50, comprising a single-piece fixation rod clamp 56, a coupling 52, a coil spring 68, and a coupling bolt 64. The single-piece fixation rod clamp has a cylindrical coupling portion 58 which is slidably disposed within an aperture 54 formed by the body of the coupling 52. Single-piece fixation rod clamp 56 is thus interconnected to and slidably disposed within the coupling 52 so as to allow 360-degree rotation of the single-piece fixation rod clamp 56 within the coupling aperture 54. The coupling bolt 64, having a head and a threaded distal end 66, is slidably disposed within a bore 70 formed in the body of coupling 52. The longitudinal axis of bore 70 is oriented perpendicular to that of the coupling aperture 54. The coupling bolt threaded distal end 66 is threadably accepted by an internally and compatibly threaded bore 26 formed in the top center of opposing plate 2 (shown in FIG. 1A) of pin vise portion 1 (shown in FIG. 1A). The single-piece fixation rod clamp 56 is thus interconnected to and rotatably disposed about pin vise portion 1. The single-piece fixation rod clamp 56 is interconnected to and rotatably disposed, with two degrees of rotational freedom, about pin vise portion 1, and so about bone pins 28 (shown in FIG. 6). The first degree of rotational freedom is provided by the rotation of single-piece fixation rod clamp 56 relative to the rod attachment portion coupling 52; the second by the rotation of the rod attachment portion coupling relative to pin vise portion 1.

The single-piece fixation rod clamp 56 is stabilized and fixed to the rod attachment portion coupling 52 by tightening the coupling bolt 64. Tightening of the coupling bolt 64 also results in the stabilization and fixation of the entire rod attachment portion 50 to the pin vise portion 1.

In a preferred embodiment, the coupling 52 has a bearing face 60 incorporating serrations 62 which extend over the entire face, and which correspond with like serrations 24 (shown in FIG. 1A) formed in the corresponding bearing face of the pin vise portion 1. The serrations may be disposed in a radial fashion to form a "star grind," or may have any type of profile known in the art. The serrations 62, 24 serve to minimize or prevent rotational slippage between the coupling 52 and the pin vise portion 1 subsequent to final tightening of the coupling bolt 64.

Figure 1B:
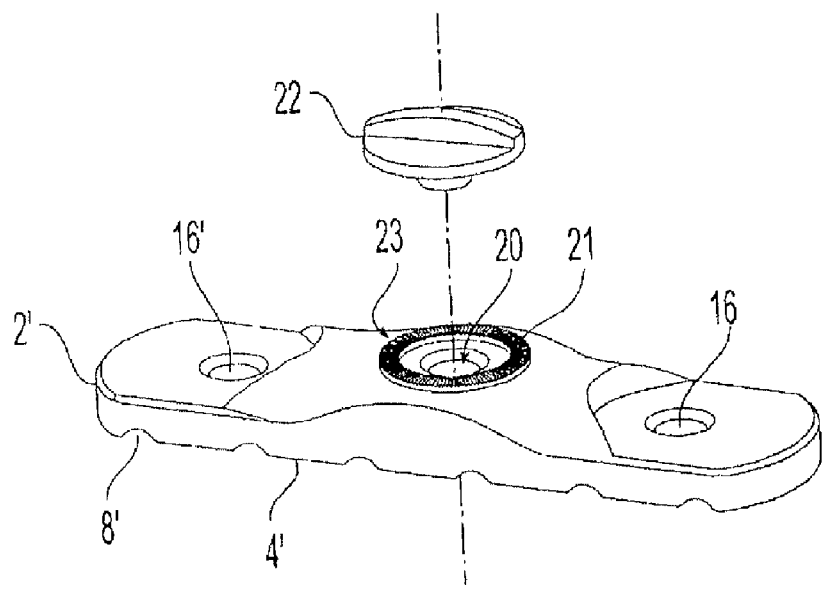
Figure 1C:
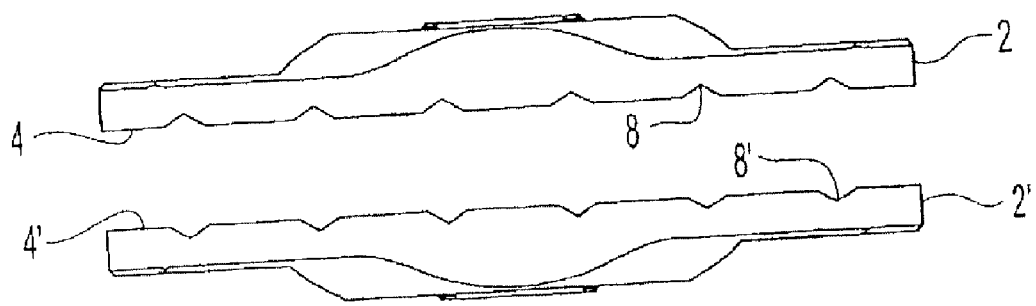

In another preferred embodiment, the pin vise portion opposing plate 2' (shown in FIG. 1B) incorporates an internally threaded bore 20, into which the coupling bolt 64 of a second rod attachment portion 50 (shown in FIG. 2) may be threaded. The bearing face 21 of the pin vise portion opposing plate 2' incorporates serrations 23 which extend over the entire face, and which correspond with like serrations 62 of the bearing face 60 of a second rod attachment portion 50 (shown in FIG. 2). The serrations 62, 23 serve to minimize or prevent rotational slippage between the second coupling 52 and the pin vise portion 1 subsequent to final tightening of the second coupling bolt 64. Two rod attachment portions 50 may thereby be installed on one pin vise portion 1 to provide the fracture site with the additional stabilizing force of a second bone fixation rod 100 (shown in FIG. 6). For those instances in which the surgeon does not require the additional stabilizing force of a second bone fixation rod, an externally threaded "star grind" cover 22 (shown in FIGS. 1A and 1B) is provided. The cover is threadably accepted by the internally threaded bore 20 of the pin vise portion opposing plate 2' (shown in FIGS. 1A and 1B). The cover 22 may have a bearing face 25 (shown in FIG. 1A) incorporating serrations 27 which extend over the entire face, and which correspond with like serrations 23 (shown in FIG. 1B) formed in the corresponding bearing face of the pin vise portion opposing plate 2'. The serrations may be disposed in a radial fashion to form a "star grind," or may have any type of profile known in the art. The serrations 23, 27 serve to minimize or prevent rotational slippage between the star grind cover 22 and the pin vise portion 1 subsequent to final tightening of the star grind cover.

As shown in FIG. 2, the coupling bolt 64 may be provided with a coil spring 68 disposed about the circumference of the bolt 64. The spring is partially slidably received within a bore 71 provided in the coupling bearing face 60. This bore is of larger diameter than coupling bore 70, which results in the creation of a circumferential ledge 72 within the coupling 52. When compressed between the rod attachment portion coupling circumferential ledge 72 and the pin vise portion 1 (shown in FIG. 1A), the spring 68 acts to provide a force tending to separate the coupling 52 and the pin vise portion 1. This force prevents engagement of the serrations 62, 24 (and serrations 62, 23 in the alternative embodiment where a second bone fixation rod is utilized) during installation, and thus enables easy relative rotation and fit-up.

Figure 4:
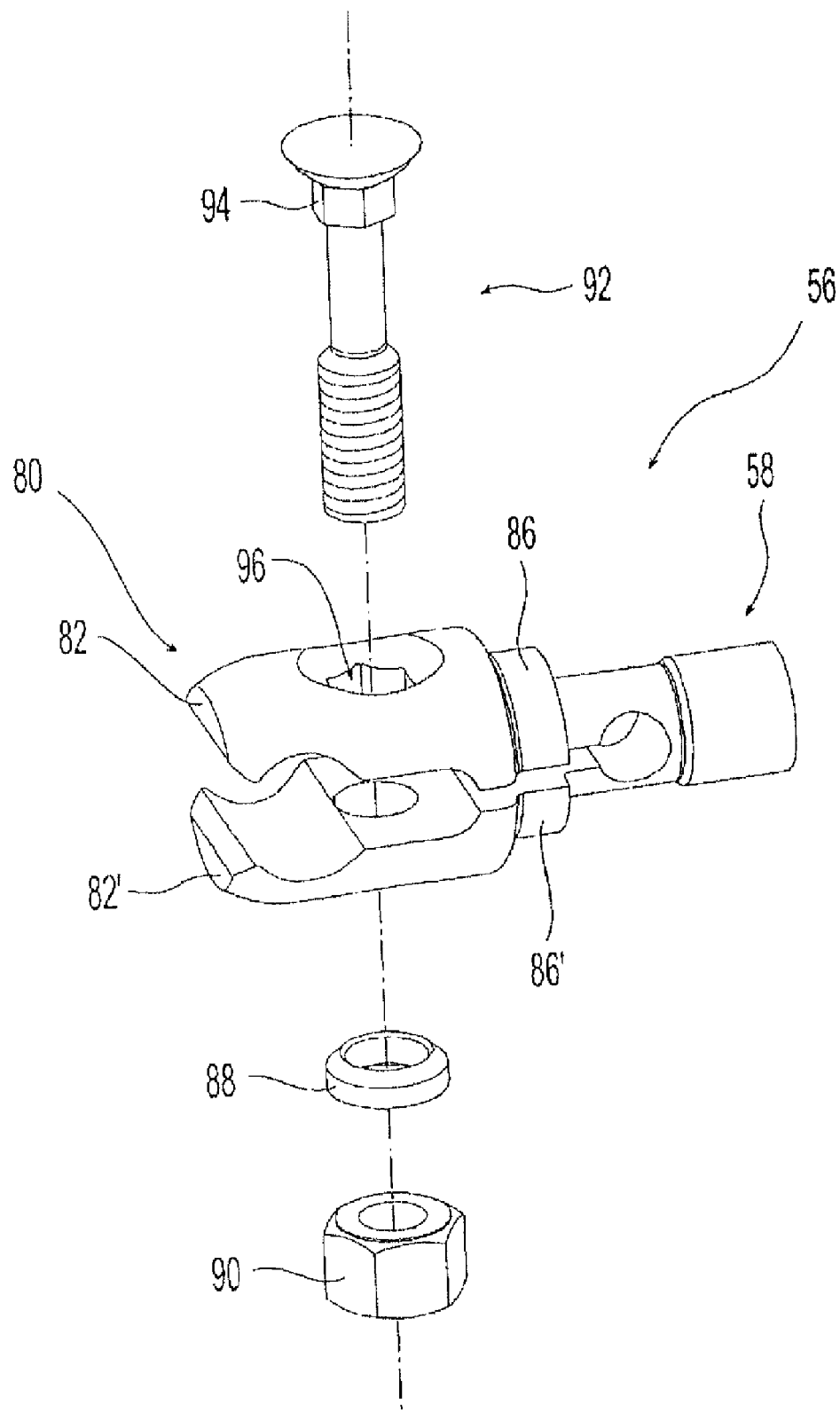
FIG. 4 is an exploded perspective view of the single piece fixation rod clamp.
Figure 5:
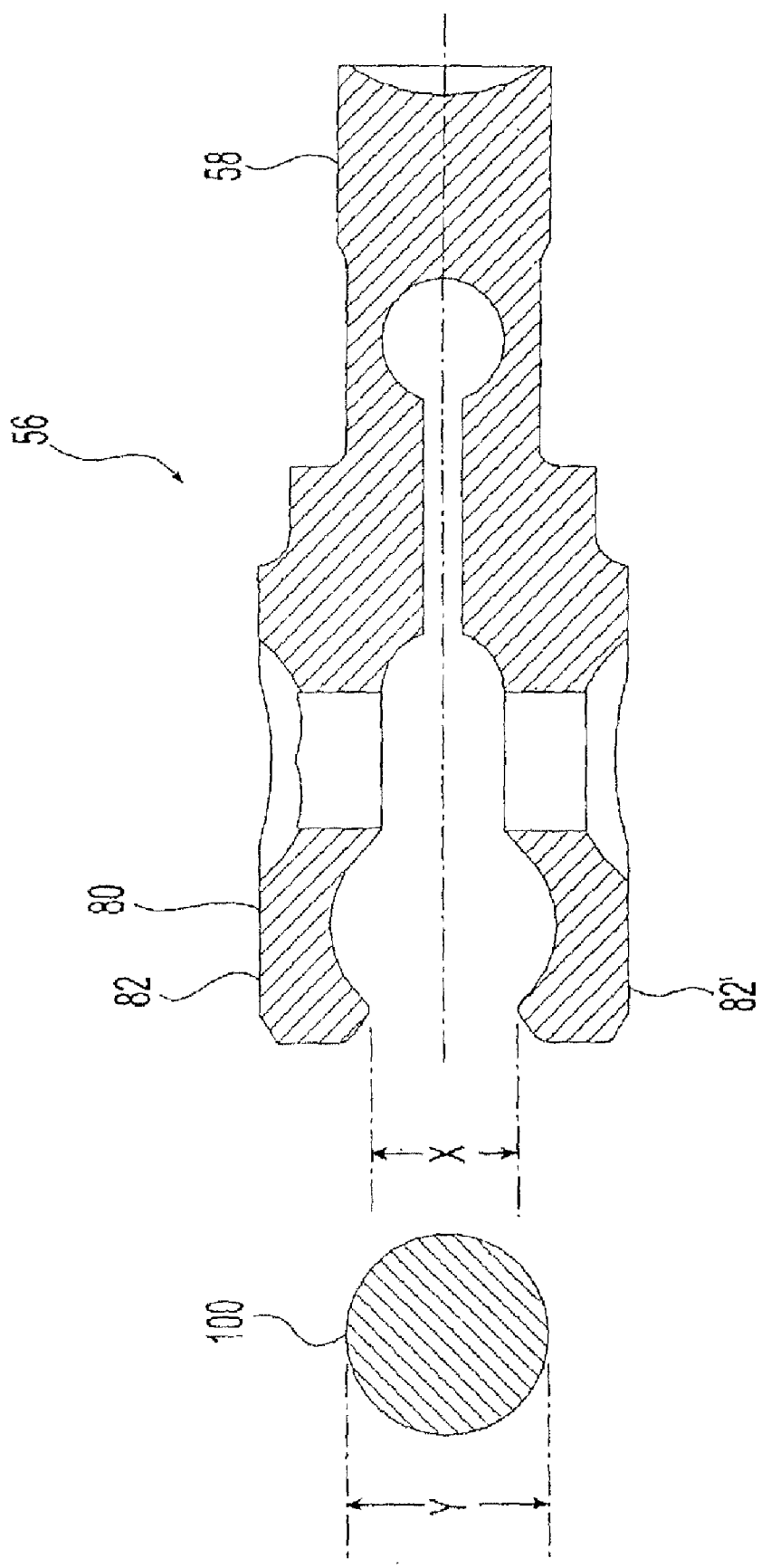
FIG. 5 is a cross-sectional view of the single-piece fixation rod clamp and a bone fixation rod.

FIG. 4 shows the details of the novel single-piece fixation rod clamp 56 of the present invention. The single-piece fixation rod clamp comprises a jaw portion 80, which further comprises a set of opposing jaws 82 and 82', each connected to a respective spring arm 86 and 86'. The spring arms converge to a smooth cylindrical coupling portion 58. Significantly, the jaw portion 80 is manufactured in a single piece, so that when the jaws 82 and 82' are positively displaced with respect to their rest position, a resulting spring force is generated which tends to force the jaws back to the rest position. The jaw portion 80 is preferably manufactured such that the initial clearance "X" between opposing jaws 82 and 82' is slightly smaller than the outside diameter "Y" of the bone fixation rod 100 (shown in FIG. 5). In this way an interference is established between jaws 82 and 82' and the bone fixation rod 100 when the bone fixation rod is initially installed into the jaw portion 80. Based on the natural spring action of the spring arms 86 and 86' adjoining the jaws 82 and 82' respectively, the relative interference between the jaws and the bone fixation rod enables the entire bone pin locking assembly (comprising pin vise portion 1 and rod attachment portion 50) to be snapped onto the bone fixation rod 100 by the operator, resulting in the capture of the bone fixation rod 100 within the rod attachment jaw portion 80. Although not fully stabilized, the spring action of the spring arms is sufficient to maintain a loose coupling of the assembly with the rod. This frees up the hands of the surgeon performing the fixation procedure.

Final stabilization of the bone fixation rod 100 within the jaw portion 80 is accomplished through the use of a bolt 92 placed through the jaw portion spring arms 86 and 86', in combination with a nut 90 (see FIG. 4). Upon tightening the nut 90 and bolt 92, the spring arms 86 and 86', and most importantly for the purposes of the invention, the adjoining jaws 82 and 82', are drawn together until the bone fixation rod 100 is firmly held between the jaws 82 and 82'. Repeated loosening and tightening of the rod attachment portion on the bone fixation rod is possible without the need for re-engagement of the rod within the jaw. In this way the surgeon may easily and multiply adjust the position of the rod attachment portion along the bone fixation rod.

An external hexagon 94 may be provided integral to the shoulder of the jaw bolt 92. This external hexagon 94 conforms to an internal hexagonal recess 96 provided within jaw portion spring arm 86. The bolt is thereby rotationally fixed to the jaw portion, such that the surgeon need only focus on threading the nut onto the bolt without having to worry about holding the bolt still.

A washer 88 may be provided between the nut 90 and jaw portion spring arm 86'. This washer can be of any design known in the art satisfactory to prevent galling of the nut and jaw portion spring arm, and to facilitate installation of nut 90 and bolt 92.

Figure 7:
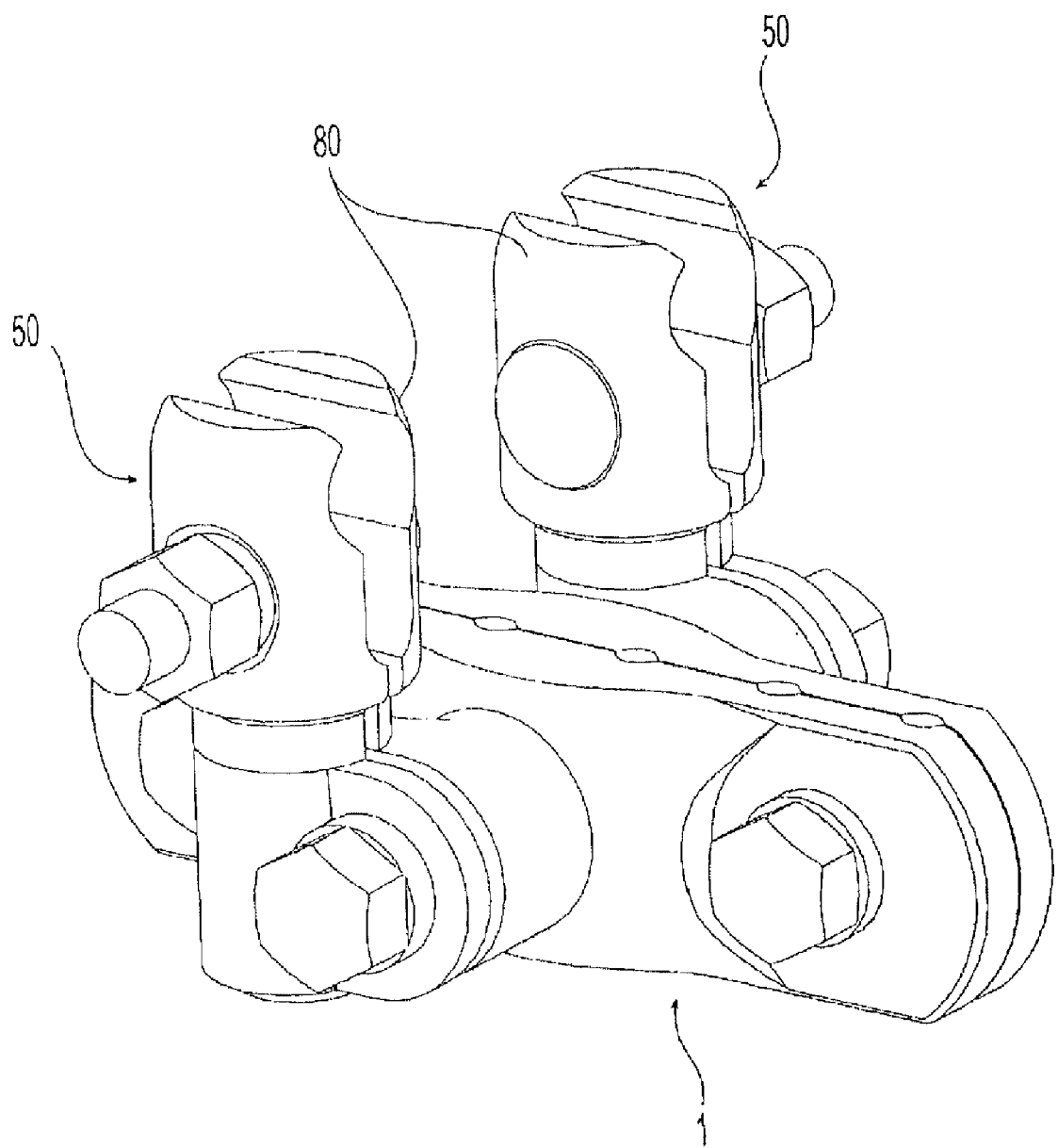
FIG. 7 is a perspective view of the stacked clamp assembly embodiment of the present invention.

FIG. 7 shows a "stacked" bone pin locking assembly which comprises one pin vise portion 1 with two associated rod attachment portions 50. Such a stacked assembly permits the surgeon to provide an additional stabilizing force, associated with a second bone fixation rod 100, to the fracture site. In this way a framework of bone fixation rods may be built about the fracture site.

Accordingly, it should be understood that the embodiments disclosed herein are merely illustrative of the principles of the invention. Various other modifications may be made by those skilled in the art which will embody the principles of the invention and fall within the spirit and the scope thereof.

What is claimed is:

1. A fixation rod clamp for coupling a bone pin locking assembly to a bone fixation rod, the clamp comprising:
   a rod attachment portion including a jaw portion and a coupling portion, the jaw portion and the coupling portion oriented to define a longitudinal axis of the rod attachment portion, the jaw portion having first and second opposing jaws, each extending parallel to the longitudinal axis from a proximal end at the coupling portion in a first direction to a free distal end, the jaws oriented to not intersect the longitudinal axis, the jaws forming an opening therebetween configured to receive the bone fixation rod, the coupling portion extending from the jaw portion along the longitudinal axis in a second direction opposite from the first direction of the opposing jaws; and a coupling having a pin vise cooperating portion to engage the bone pin locking assembly and a clamp cooperating portion configured to receive the coupling portion along the longitudinal axis in the second direction, wherein the jaw portion is configured to engage the bone fixation rod when the bone fixation rod is located within the opposing jaws to thereby mechanically couple the bone pin locking assembly to the bone fixation rod.

2. The fixation rod clamp of claim 1, wherein the first opposing jaw has a first spring constant, and the second opposing jaw has a second spring constant, and wherein when at least one of the first and second opposing jaws is displaced from a rest position, a resulting spring force is generated in the at least one jaw, urging the displaced jaw back toward the rest position.

3. The fixation rod clamp of claim 2, wherein when the bone fixation rod is inserted into the jaw portion, the spring force in the at least one opposing jaw contributes to the mechanical coupling of the bone pin locking assembly to the bone fixation rod.

4. The fixation rod clamp of claim 1, wherein the clamp is configured to have a locked position which substantially prevents movement of the clamp along the bone fixation rod.

5. The fixation rod clamp of claim 1, wherein the jaw portion engages and provisionally holds the bone fixation rod when the bone fixation rod is located in the jaw portion.

6. A fixation member clamp for coupling to a first bone fixation member, the clamp comprising:

a fixation member attachment portion including a jaw portion and a coupling portion, the jaw portion and the coupling portion oriented to define a longitudinal axis of the fixation member, the jaw portion having first and second opposing jaws, each extending parallel to the longitudinal axis from a proximal end at the coupling portion in a first direction to a free distal end, the jaws oriented to not intersect the longitudinal axis, the jaws forming an opening therebetween configured to receive the first bone fixation member, the coupling portion forming an extension extending along the longitudinal axis in an opposite direction from the first direction of the opposing jaws; and a locking assembly comprising a coupling and a locking portion, the coupling forming an aperture to receive the extension of the coupling portion along the longitudinal axis in the second direction, the locking portion configured to engage a pin vise portion, wherein the fixation member attachment portion is configured to engage the first bone fixation member when the first bone fixation member is located between the opposing jaws of the jaw portion to thereby mechanically couple the bone fixation member to the locking assembly, and wherein the coupling portion of the fixation member attachment portion and the locking assembly are configured to allow at least one degree of rotational freedom of the jaw portion with respect to the locking assembly.

7. A fixation rod clamp for coupling a bone pin locking assembly to a bone fixation rod, the clamp comprising:

a rod attachment portion including a jaw portion and a coupling portion, the jaw portion and the coupling portion oriented to define a longitudinal axis of the rod attachment portion, the jaw portion having first and second opposing jaws, each extending parallel to the longitudinal axis from a proximal end at the coupling portion in a first direction to a free distal end, the first and second jaws configured to receive the bone fixation rod, the jaws oriented to not intersect the longitudinal axis, the coupling portion joined with the jaw portion and extending along the longitudinal axis in a second direction opposite the first direction from the jaw portion; and a coupling having a pin vise cooperating portion to engage the bone pin locking assembly and a clamp cooperating portion configured to receive the coupling portion along the longitudinal axis.

8. The fixation rod clamp of claim 7, wherein the first opposing jaw has a first spring constant, and the second opposing jaw has a second spring constant, and wherein when at least one of the first and second opposing jaws is displaced from a rest position, a resulting spring force is generated in the at least one jaw, urging the displaced jaw back toward the rest position.

9. The fixation rod clamp of claim 8, wherein when the bone fixation rod is inserted into the jaw portion, the spring force in the at least one opposing jaw contributes to the mechanical coupling of the bone pin locking assembly to the bone fixation rod.

10. The fixation rod clamp of claim 7, wherein the clamp is configured to have a locked position which substantially prevents movement of the clamp along the bone fixation rod.

11. The fixation rod clamp of claim 7, wherein the jaw portion engages and provisionally holds the bone fixation rod when the bone fixation rod is located in the jaw portion.

* * * * *